US008016803B2

(12) United States Patent
Mueller et al.

(10) Patent No.: US 8,016,803 B2
(45) Date of Patent: *Sep. 13, 2011

(54) ABSORBENT ARTICLE WITH URINE-PERMEABLE COVERSHEET

(75) Inventors: Joerg Mueller, Karben (DE); Cornelia Martynus, Nidderau-Ostheim (DE); Ralf Geilich, Eppstein (DE); Simone Seeboth, Schwalbach (DE); Ekaterina Anatolyevna Ponomarenko, Bad Soden (DE); Michael I. Divo, Friedrichsdorf (DE)

(73) Assignee: The Procter & Gamble Company, Cincinnati, OH (US)

( * ) Notice: Subject to any disclaimer, the term of this patent is extended or adjusted under 35 U.S.C. 154(b) by 172 days.

This patent is subject to a terminal disclaimer.

(21) Appl. No.: 11/224,779

(22) Filed: Sep. 13, 2005

(65) Prior Publication Data

US 2006/0058766 A1    Mar. 16, 2006

Related U.S. Application Data

(60) Provisional application No. 60/609,393, filed on Sep. 13, 2004.

(51) Int. Cl.
*A61F 13/15* (2006.01)

(52) U.S. Cl. ......... 604/385.08; 604/385.19; 604/385.09; 604/385.23; 604/385.101; 604/378; 604/382; 604/385.24

(58) Field of Classification Search ............ 604/348, 604/385.19, 385.08, 385.01, 385.23
See application file for complete search history.

(56) References Cited

U.S. PATENT DOCUMENTS

| | | | |
|---|---|---|---|
| 3,860,003 A | 1/1975 | Buell | |
| 4,573,986 A | 3/1986 | Minetola et al. | |
| 4,695,278 A | 9/1987 | Lawson | |
| 4,795,454 A | 1/1989 | Dragoo | |
| 4,808,178 A | 2/1989 | Aziz et al. | |
| 4,950,262 A * | 8/1990 | Takagi | 604/385.101 |
| 5,062,840 A * | 11/1991 | Holt et al. | 604/385.19 |
| 5,462,541 A * | 10/1995 | Bruemmer et al. | 604/391 |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe et al. | |
| 5,779,690 A * | 7/1998 | Gustafsson et al. | 604/385.19 |
| 5,817,086 A * | 10/1998 | Kling | 604/385.19 |

(Continued)

FOREIGN PATENT DOCUMENTS

EP    0 359 410 A1    3/1990

(Continued)

OTHER PUBLICATIONS

Definition of "free", Merriam-Webster OnLine.*

(Continued)

*Primary Examiner* — Jacqueline F Stephens
(74) *Attorney, Agent, or Firm* — John G. Powell; William E. Gallagher (57) ABSTRACT

An absorbent article having a backsheet, an absorbent core, a topsheet, and a genital coversheet. The topsheet has an opening positioned to allow exuded fecal material to pass therethrough when the article is worn by a wearer. The genital coversheet is positioned across a portion of the aperture and covers the wearer's genitals. A void space is formed between the genital coversheet and the absorbent core and a void space is formed between the topsheet and the absorbent core.

17 Claims, 5 Drawing Sheets

U.S. PATENT DOCUMENTS

| | | | |
|---|---|---|---|
| 5,853,403 A | 12/1998 | Tanzer et al. | |
| 6,013,065 A * | 1/2000 | Suzuki et al. | 604/385.27 |
| 6,132,409 A * | 10/2000 | Vogt et al. | 604/348 |
| 6,328,724 B1 * | 12/2001 | Ronnberg et al. | 604/385.24 |
| 6,402,729 B1 * | 6/2002 | Boberg et al. | 604/385.28 |
| 6,508,798 B1 * | 1/2003 | Widlund et al. | 604/385.27 |
| 6,786,895 B1 * | 9/2004 | Schmitz | 604/385.28 |
| 7,175,613 B2 * | 2/2007 | Sugiyama et al. | 604/385.14 |
| 2001/0023342 A1 | 9/2001 | Suekane | |
| 2002/0099351 A1 * | 7/2002 | Onishi et al. | 604/385.19 |
| 2004/0039363 A1 * | 2/2004 | Sugiyama et al. | 604/385.101 |
| 2007/0078420 A1 * | 4/2007 | Sugiyama et al. | 604/361 |

FOREIGN PATENT DOCUMENTS

| | | |
|---|---|---|
| EP | 0 357 298 B1 | 11/1990 |
| EP | 1 064 899 A1 | 1/2001 |
| EP | 1 201 212 A2 | 5/2002 |
| GB | 2 268 073 A | 1/1994 |
| JP | 04-218157 A | 8/1992 |
| WO | WO 95/24173 A2 | 9/1995 |
| WO | WO 0200154 A1 * | 1/2002 |

OTHER PUBLICATIONS

Definitions of "component" and "distinct", Webster's Third New International Dictionary, unabridged.*

* cited by examiner

ABSORBENT ARTICLE WITH URINE-PERMEABLE COVERSHEET

CROSS REFERENCE TO RELATED APPLICATION

This application claims the benefit of U.S. Provisional Application No. 60/609,393 filed Sep. 13, 2004.

FIELD OF THE INVENTION

This invention is directed to an absorbent article, preferably a diaper or training pants, having a backsheet, an absorbent core and a topsheet, provided with at least one opening adapted to receive fecal material, comprising also a genital coversheet, which in use covers the genitals, and which is positioned in, under or above part of the opening, such that a void space is present between the topsheet and the absorbent core.

BACKGROUND OF THE INVENTION

It is well known that fecal material is often difficult to remove from the skin of the user, in particular on sensitive skin such as that of young babies and the skin around the genitals. Moreover, it is well known that fecal material on the skin can cause irritation and redness of the skin and sometimes even dermatitis.

One of the solutions to reduce the fecal material on the skin is to provide a means to isolate the fecal material immediately after discharge, away from the skin. For example, diapers with a topsheet with one or more openings, through which the feces can pass to a void space between the topsheet and the absorbent core, have been developed. The fecal material is then stored underneath this topsheet, away from the skin.

However, occasionally still some fecal material may transfer back onto the skin including on the genitals.

Therefore, an absorbent article with a genital coversheet, which protects in use the genitals from being soiled by the fecal material, has been developed. This cover is typically only present in the areas of the topsheet and of the opening, which are in proximity with the genitals (i.e., the front of the opening in the topsheet of the diaper), to allow sufficient open space to pass the fecal material through. The cover may be an integral part of said topsheet with the opening, or it may be an additional component (sheet) attached to for example the topsheet with the opening.

Preferably, the genital coversheet is such that it forms a pocket in use, which can partially enclose the genitals.

SUMMARY OF THE INVENTION

An absorbent article has a backsheet, an absorbent core, a topsheet, and a genital coversheet. The topsheet has an opening positioned to allow exuded fecal material to pass therethrough when the article is worn by a wearer. The genital coversheet is positioned across a portion of the opening and covers the wearer's genitals. A void space is formed between the genital coversheet and the absorbent core and a void space is formed between the topsheet and the absorbent core.

DETAILED DESCRIPTION OF THE INVENTION

As used herein, the following terms have the following meanings:

As used herein, 'absorbent article' means any article that can absorb body fluids and is suitable to be placed in close proximity to the genitals of the user, including in particular an adult or infant diaper and so-called training or pull-on pants.

As used herein 'front region' and 'back region' refer to the two regions, which are in use, respectively, closest to the front of the wearer and the back of the wearer.

As used herein the 'crotch side portion' is the portion of the topsheet between the longitudinal side edge of the opening and the longitudinal side edge of the topsheet, and the crotch side portion may thus be part of the front region and/or the back region.

As used herein, a 'void space' is a cavity in the article present in at least the relaxed state, which serves to accept and contain bodily exudates such as fecal material, typically being at least 5 $cm^3$ in the relaxed state.

When used herein, 'longitudinal' is the direction running substantially parallel to the maximum linear dimension of the component, typically parallel to the longitudinal axis of the article, and includes directions within 30° of this parallel, when applicable.

The 'lateral' or 'transverse' direction is perpendicular to the longitudinal direction and in the same plane of the majority of the article and the longitudinal axis and includes directions within 30° of the perpendicular, when applicable.

'Extendibility' and 'extendable', when used herein, means that the width or length of the component (in its relaxed state) can be increased.

As used herein, the term 'attached' encompasses configurations wherein a first element is directly secured to another element by affixing the element directly to a second element.

As used herein, the term 'joined' or 'connected' encompasses configurations wherein a first element is indirectly secured to a second element by affixing the first element to a third, intermediate member(s), which in turn is affixed to the second element.

As used herein 'stretched' or 'stretched state' means that the article or topsheet thereof is stretched to its maximum length, which is typically determined by the length of a non-elastically extendable component which is part thereof, e.g., the backsheet or the non-elastically extendable material of the topsheet.

As used herein 'relaxed' or 'relaxed state' means the state in which no forces are applied to the article or component thereof (other than naturally occurring forces such as gravity), when the article is laid on a horizontal surface, such that the transverse front and back edge are flat on the horizontal surface and the transverse centre line or axis is on the horizontal surface.

As used herein, 'elasticated' means typically, that the component consists of or comprises elastic material, which is elastic in at least one direction. 'Non-elasticated' when used herein means that the component does not comprise any elastic material.

As used herein, 'along' means 'at least partially substantially parallel to and adjacent to'. Adjacent includes 'in close proximity with' and 'in contact with'.

As used herein, 'opening in the topsheet' means an area completely circumscribed by the topsheet, but where the topsheet material is not present, and which is large enough to receive fecal material, typically being at least 2 cm long or wide, or having a surface area of at least 2 cm$^2$.

As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

In a first embodiment, the absorbent article of the invention comprises one or more opening(s), preferably a single opening, for the reception of fecal material and a genital coversheet. Preferably, the opening is in the form of a slit opening. The opening is preferably present in (part of) the front region of the topsheet (in use toward the front of the user) and in (part of) the back region of the topsheet.

Preferably, the topsheet has a slit opening, which has a longitudinal dimension (length) substantially parallel to the longitudinal axis of the topsheet and of the diaper.

It is preferred that (in the stretched state) the opening (or openings) of the topsheet is (are) configured such that from 20% to 40%, or more preferably from 20% to 30% of the length of the opening (or total length of the openings) extends from the transverse axis of the topsheet toward the front edge of the topsheet, and the remaining percentage extends toward the back edge of the topsheet.

The dimensions and exact shape of the opening(s) may vary, depending on the size of the topsheet and/or the absorbent article. For example, in a preferred embodiment the opening is in the form of a slit opening with substantially parallel longitudinal side edges, which are connected in the front and back by V-shaped or rounded V-shaped (as shown hereinafter) front and back edges, wherein both the front and back V-shaped edges comprise two angled edges.

Figure 4:
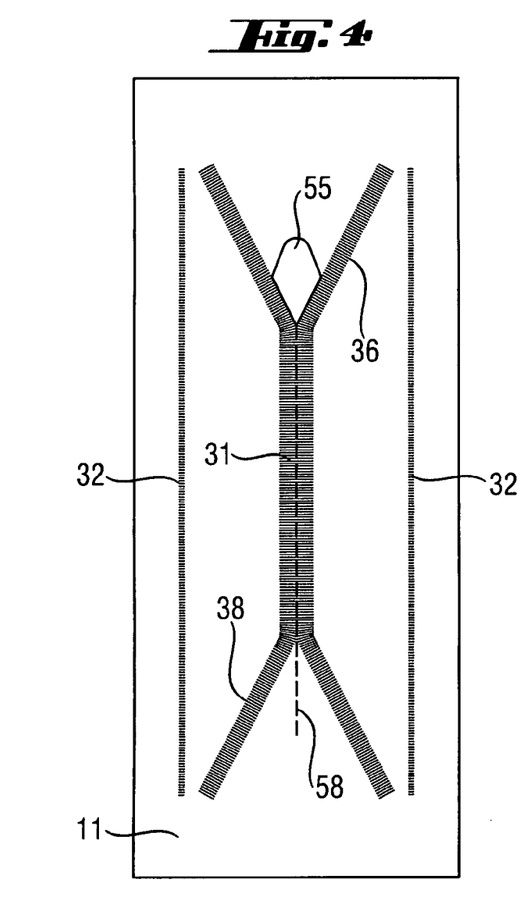
FIGS. 4 and 5 show how the slit opening may be cut in the topsheet.
Figure 5:
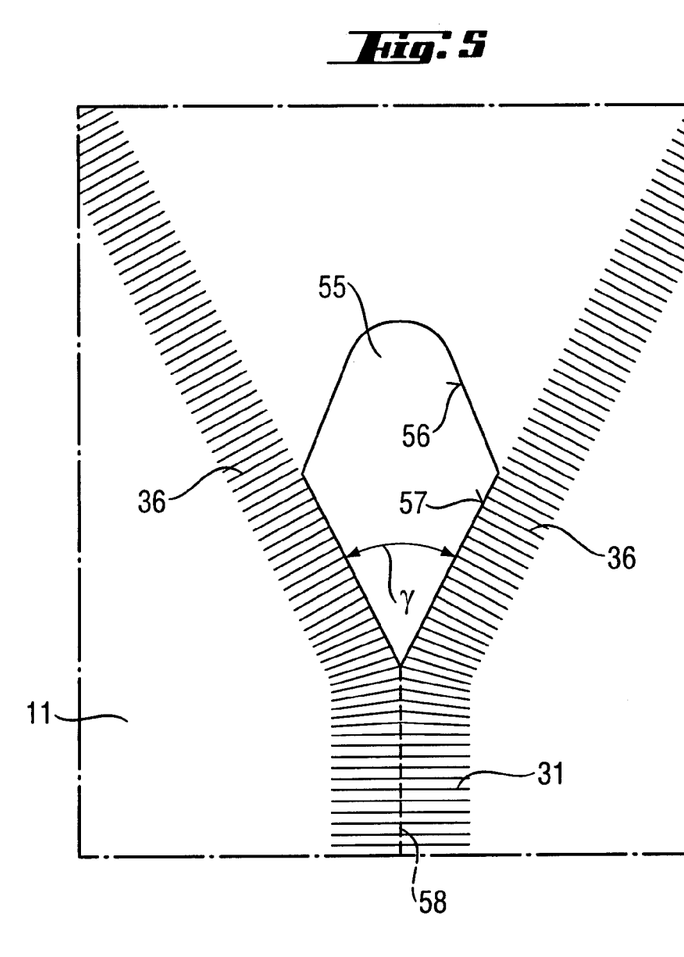

In a preferred embodiment, the front V-shaped edges have a larger angle than the back V-shaped edges. Preferably, the front V-shaped edges have an angle of 20° to 140°, preferably from 45° to 65°, most preferably from 55° to 60°, as described hereinafter and can be seen from FIGS. 1 and 2. As shown in FIGS. 4 and 5, the slit opening may optionally extend into an additional cut-out area 55 which is for example diamond-shaped, as described hereinafter.

The maximum length of the slit opening may be for example 40% to 90% or more preferably 50% to 80%, or even more preferably about 60% to 70%, of the total length of the absorbent article.

It may be preferred, in particular for size 4 diapers with a maximum topsheet length of between 45 cm and 55 cm, typically between 48 cm and 52 cm, that the length of the single slit opening, when the diaper is in the stretched state, is from 20 cm to 40 cm, or even from 25 cm to 35 cm, or even from 28 cm to 32 cm.

The average width of the opening, in the stretched state, is preferably from 5% to 30%, or more preferably 10% to 25%, of the average width of the topsheet (including opening width), or for example for a size 4 diaper, 15 mm to 60 mm, more preferably from 20 mm to 40 mm.

In a second embodiment, the absorbent article comprises a backsheet and an absorbent core and a body-facing liner, which is apertured, comprising a multitude of micro-apertures, as described hereinafter (referred to hereinafter also as a sublayer for the first embodiment of the invention), and for example described in EP 0 714 272. The genital coversheet is then present above this apertured body-facing liner, between the skin of the user and the body-facing liner. Preferably, the genital coversheet is present in only the front region of the absorbent article, above the front region of the body-facing liner. The genital coversheet is preferably not completely attached to the body-facing liner, or more preferably not attached to the body-facing liner. The genital coversheet is then spaced apart from the body-facing liner by spacing means, to allow formation in use of a pocket by the genital coversheet, around the genitals. To this purpose, the absorbent article may comprise a pair of longitudinally extending cuffs, placed along the longitudinal side edges of the absorbent article, and extending in the z-direction from the X-Y plane of the article, and the genital coversheet may then be attached to these cuffs, for example, attached to the outer surface of the cuffs (this being the surface which in use is not in contact with the skin).

In the first embodiment of the invention, relating to an absorbent article with a topsheet with one or more openings, as referred to above, the absorbent article of the invention comprises a genital coversheet that is present under, in or above the opening in the topsheet, typically only that part of the opening that is in close proximity with the genitals during use, i.e., the front region of the opening. Preferably, the maximum length of the part of the genital coversheet that is present above, in or under the opening genital is 10% to 50% of the maximum length of the opening, preferred 10% to 30%, or more preferably 13% to 28% or even more preferably 17% to 27%. In other words, at the most 50% of the maximum length of the opening is 'covered' by the longest part of the genital coversheet, but at least 10% of the maximum length of the opening is covered by the longest part of the genital coversheet.

Preferably, the genital cover sheet has a substantially transverse edge above, in or under the opening which is not straight, but preferably curved or V-shaped (arrow-shaped), having the centre point of the curved edge or of the V-shaped edge closer to the front of the article than the remaining part of the curved edge or V-shaped edge. Then, the length of the part of the genital coversheet from this centre point to the front of the opening is preferably 10% to 30% of the maximum length of the opening, more preferably 15% to 25%, or even to 20%.

When the genital coversheet is present under the topsheet and below the opening, thus between the topsheet and the absorbent core, then, the genital coversheet is typically not attached to the absorbent core, to ensure the creation of a maximum void space for fecal material between the topsheet and the absorbent core and between the genital coversheet and the absorbent core.

The genital coversheet may be attached to the absorbent article by any means, including adhesive bonding, heat bonding, pressure bonding, and including various bonding patterns, such as a longitudinal line or a longitudinal line formed from individual transverse lines or dots, etc.

Preferably, the genital coversheet is partially attached to the topsheet, forming thereby attachment areas and non-attached area(s). (Some of) the non-attached area(s) may then form the protective genital cover for the genitals, typically in the form of a pocket.

In a preferred embodiment, the genital coversheet is extendable, either longitudinally or transversely or both, so that the pressure of the genitals onto the genital coversheet causes the genital coversheet to extend and form a pocket around the genitals. The genital coversheet may be elastically extendable, or preferably, the genital coversheet may be non-elastically extendable, in the longitudinal and/or, more preferably, in the transverse direction. To this purpose, the genital coversheet is preferably attached, for example to the topsheet, with a pair of opposing attachment areas, with thereinbetween one or more unattached area(s), as described above, whereby the average width of the unattached area(s) of the genital coversheet, between the pair of attachment area(s), is larger than the average distance (width) between the two attachment areas, preferably at least 1.2 times larger, or even 1.5 times larger.

In yet another embodiment of the invention, the genital coversheet is an integral part of the topsheet with the opening. Then, the genital coversheet is herein referred to as a genital cover portion of the topsheet. This integral genital coversheet or genital cover portion is then urine-permeable, as described hereinafter, and the remaining part of the topsheet (the feces-retaining portion) except for the opening is urine-impermeable, as described hereinafter. The urine-permeable genital cover portion is present in the front region of the topsheet, preferably between the front edge of the topsheet and the front edge of the opening, while the back region of the topsheet comprises said opening and the feces-retaining portion.

Then, the genital cover portion typically forms the front 10% to 50%, or more preferably 15% to 30%, or more preferably 15% to 20%, of the surface area of the topsheet, while the fecal-material retaining portion, being the back portion of the topsheet, forms the remaining percentage of the surface area of the topsheet.

It may also be preferred that the genital cover portion of the topsheet is extendable, preferably (at least) in the transverse direction.

In another embodiment, the genital coversheet extends over the whole length of the opening and comprises also an opening, for receiving fecal material.

The genital coversheet is preferably urine-permeable. Urine-permeability can be determined by the Strike Through test, EDANA test method 150.3-96, which is modified in that it applies two gushes of 5 ml to the same sample with a waiting time of 60 seconds between the two gushes (without changing the absorbent pad) and in that the absorbent pad consists of 10 plies of filter paper, rather than five plies; the filter paper used may be Ahlstroem grade 989, or equivalent; the pick-up paper may be Ahlstroem Grade 632 or equivalent. This modified EDANA test method provides the strike through times of the first gush and second gush, each of which is an average of the values obtained in three tests.

Typically, the genital coversheet has an average first gush strike through time of less than 7 seconds, but typically less than 5 seconds, or more preferably less than 3 seconds, and most preferably between 1 and 3 seconds or most preferably between 1 and 2 seconds. Preferably, the genital coversheet has a second gush strike through time of less than 9 seconds, preferably less than 7 seconds, or more preferably even less than 5 seconds, and preferably between 1 and 7 seconds or more preferably between 2 and 5 seconds, or even more preferably between 1 and 5, or even 3 seconds.

Preferably, the genital coversheet does not allow moisture to pass back to the skin, and therefore, it preferably has a low rewet. This can be determined by the Wetback Test, EDANA test method 151.3-02, under 23° C. and 50% humidity test conditions, as specified in the EDANA test method, and using a filter paper with a loading factor of 3.30, as specified therein, and resulting in average rewet values, which are an average of 3 test results (the filter paper used may be as specified above). Preferably the genital coversheet has an average rewet value of less than 0.8 g, preferably less than 0.5 g, more preferably less than 0.3 g, or even more preferably less than 0.2 g or even less than 0.15 g.

Also it may be preferred that the genital coversheet can let low viscosity fecal material pass through and entrap it, thereby protecting the genitals from said fecal material. It is preferred therefore that the genital coversheet is formed from materials with large pores, and large caliper, e.g., a mean pore size of 50 to 400 microns, or even more preferably from 100 to 300 microns, and an average caliper (measured under compression of 0.3 psi (approximately 2 kPa)) of 0.5 mm to 1.5 mm, preferably 0.7 mm to 1 mm, such as carded resin-bonded or through-air bonded nonwovens made of for example PET fiber.

Preferred genital coversheets are hydrophilic, or treated with a hydrophilising agent to render them hydrophilic. Preferred materials for the genital coversheet are nonwoven and woven materials comprising hydrophilic fibers and/or nonwoven or woven materials treated with a hydrophilising agent, e.g., a surfactant.

A preferred genital coversheet is also soft to the touch. Therefore, it may be preferred that at least the surface in contact with the genitals is formed by a carded or spunbond material.

Preferred are for example spunbond nonwovens, laminates of spunbond nonwovens (S) and meltblown nonwovens (M), such as SM and SMMS laminates, or carded nonwovens, or apertured formed films, such as for example described in WO 96/00549, which each may be coated with a hydrophilising agent, e.g., a surfactant.

Also highly preferred are carded nonwoven materials, with preferably an average caliper (measured under compression of 0.3 psi (approximately 2 kPa)) of at least 0.3 mm, preferably at least 0.5 mm, even more preferably 0.7 mm, and/or with a mean pore size of from 100 microns to 300 microns.

It may be preferred that the genital coversheet or a part thereof is colored (e.g., other then the normal white color of known diapers), comprising a coloring agent, and/or that the genital coversheet is opaque, comprising an opacifying agent. This helps to mask the fecal material deposited in the absorbent article and present under the genital coversheet.

Preferably, the topsheet has, typically adjacent to, or in close proximity with, each longitudinal side edge of the opening a primary elasticated area, to form typically a pair of opposing, preferably at least partially parallel, elasticated areas, such as described in EP 1 201 212.

It may be preferred that the genital coversheet is attached to the topsheet by at least two attachment areas that are along, either directly adjacent or not, part of the longitudinal side edges of the opening.

When the genital coversheet is attached to the topsheet with at least a pair of opposing attachment areas, then the attachment areas are preferably not located where the primary elasticated areas are located, but preferably in close proximity to said primary elasticated areas.

It may be preferred that the topsheet comprises these attachment areas (where the genital coversheet is attached to the topsheet) along the opposing longitudinal side edges of the (slit) opening in said topsheet, but spaced apart from these edges, preferably by about 2 mm to 20 mm, more preferably by about 5 mm to 15 mm.

An elasticated area in the topsheet may be formed from a multitude of thin strands of elastic material or for example from a single band of elastic material.

The primary elasticated areas extend preferably from said side edges of the opening(s) toward or completely to the front and back edge of the topsheet. Thus, the primary elasticated areas are preferably longer than the opening. It is preferred that the elasticated area is positioned over the full length of the topsheet, or at least the part of the topsheet which in use is intended to receive body exudates, typically the topsheet minus the parts thereof which form (part of) the waist bands.

The width of the elasticated areas on the topsheet will vary, typically depending on the exact dimensions of the topsheet and/or the article. For example, for size 4 diapers as described above, a primary elasticated area, in the stretched state, may be an elastic band, or a multitude of elastic strands, having an average width of about 3 mm to 50 mm, preferably 3 mm to 40 mm, or even more preferably 3 mm, or even 5 mm to 20 mm.

Also, the length of the primary elasticated area will typically depend on the size of the topsheet and/or the article. For example, for a size 4 diaper as described above the average length of the elasticated area in the stretched state, may preferably be at least 35 cm, preferably from 35 cm to 45 cm.

The primary elasticated area is preferably shaped such that it has a centre portion that is substantially parallel to the centre portion of the opposing primary elasticated area. Each of the two centre portions has a length L2, which is preferably 30% to 70% of the total length L1 of a corresponding elasticated area, and preferably about 40% to 80% of the maximum length of the opening; it is preferred that the total length of the elasticated area is about 70% to 90%, or preferably from about 80% to 90% or preferably about 85% of the maximum length of the topsheet.

It is preferred that the front end portions of the two opposing primary elasticated areas bend away from one another (in the plane of the topsheet), so that the distance between the end edges of the opposing front end portions of the two opposing elastic areas is larger that the distance between the centre portions of the two opposing elastic areas, and similarly, the distance between the end edges of the opposing back end portions of the two opposing elastic areas is larger that the distance between the centre portions of the two opposing elastic areas. Then, the front end portion of a primary elasticated area has typically an angle with a longitudinal line through the centre portion of the elasticated area and parallel to the longitudinal axis of the topsheet, said angle being between 10° and 40°, or preferably between 17° to 35°, or even more preferably between 20° and 35°. Then, the back end portion of each of the primary elasticated areas has also preferably an angle with a longitudinal line through the centre portion of the elasticated area and parallel to the longitudinal axis of the topsheet, said angle being between 10° and 40°, or preferably between 17° to 35°, or even more preferably between 20° and 35°.

When both front end portions and both back end portions have an angle as above, then the primary elasticated areas have, as is herein referred to, an X-shape, and a preferred X-shape is exemplified in FIGS. 1 and 2, as described hereinafter.

It may be that the front end and/or the back end and/or the centre portion of an elasticated area is (are) curved rather than straight, and then the angles above are determined by the angle of the tangent line through the centre point of the front end and/or the back end, with the line parallel to the longitudinal axis of the topsheet and tangent to the centre point of the centre portion of the elasticated area.

Preferably, the absorbent article comprises in each crotch side portion (i.e., the portion of the topsheet between the longitudinal side edge of the topsheet and the longitudinal side edge of the opening) a secondary elasticated area, and each secondary elasticized area preferably has an overall curvature, curving away from the primary elasticated area of the same crotch side portion. The overall curvature is the curved line through the two end points of a secondary elasticated area and through the point on the same secondary elasticated area that is closest to the primary elasticated area of the same crotch side portion (herein referred to as 'closest point'), whereby the two end points are always farther away from the primary elasticated area than said closest point, or in other words, an end point is never the closest point. An end point of a secondary elasticated area is herein the point of the transverse end edge of the secondary elasticated area, which is transversely closest to the longitudinal side edge of the topsheet, and transversely farthest away from a primary elasticated area.

This curved line has a radius R of between 0.3 times the length of the absorbent article (L) to 3.2 times the length of the article or preferably 0.4 times the length of the article to 2.8 times the length of the article.

Thus, the secondary elasticated area may be a perfect curved line, a curved line with an inflection point (as shown in for example FIG. 2), or two (straight) lines connected with an angle with one another ('angled'), etc.

The transverse distance from this closest point to the primary elasticated area is preferably at least 0.5 mm, preferably between 0.5 mm and 30 mm, or even more preferably between 3.0 mm and 20 mm.

The end points of each secondary elasticated area are preferably close to the longitudinal side edges of the topsheet, but preferably not in contact with the longitudinal side edges of the topsheet, preferably the transverse distance between the longitudinal side edges and an end point being at least 5.0 mm, preferably at least 10 mm. Preferably, the end points of a secondary elasticated area are close to the transverse edge of the topsheet, but preferably not in contact with the transverse end edge of the topsheet, the longitudinal distance between an end point and the transverse end edge of the topsheet being preferably between 1% and 20% of the total length of the topsheet and/or of the article, more preferably between 5% and 15% or even between 9% and 13% of the total length of the topsheet and/or the article.

Preferably, the average transverse distance between the primary and secondary elasticated areas of a crotch side portion is at least 15 mm, or more preferably at least 20 mm or even more preferably at least 25 mm, this average being the average of three distances, namely the transverse distance from the closest point (of the secondary elasticated area) to the primary elasticated area, the transverse distance from the front end point (of the secondary elasticated area) to the primary elasticated area, and the transverse distance from the back end point (of the secondary elasticated area) to the primary elasticated area, i.e., the three transverse distances of the three points that determine the curvature of the secondary elasticated area.

Preferably, the secondary elasticated area does not comprise any angles and it is curved over its full length, with a single curvature, optionally with an inflection point.

The average width of a secondary elasticated area, e.g., a multitude of strands or a single band of elastic material, is from 0.5 mm to 20 mm or even from 0.5 mm to 10 mm.

The length of a secondary elasticated area will depend on the length of the article and the topsheet thereof, and the elastic cross machine direction (CD) force required, e.g., the curvature required and the distance to the primary elasticated area required, as mentioned above.

The topsheet comprises preferably also one or more tertiary elasticated areas. A tertiary elasticated area is then present between a secondary elasticated area and a longitudinal side edge of the topsheet, and preferably spaced apart from the closest secondary elasticated area with an average transverse distance of at least 5 mm, or preferably at least 10 mm, or even more preferably at least 15 mm.

The tertiary elasticated areas are preferably also curved, with an overall curvature as described above for the secondary elasticated area, but whereby the minimum radius is 0.1 times the length of the article.

Preferably, the elasticated areas are formed by attaching an elasticated material in the stretched state or partially being in the stretched state to the topsheet, or to one or more carrier material(s), which is (are) then subsequently attached to the topsheet.

The elastic materials are typically in the form of a multitude of strands or a single band with an average thickness (e.g., gauge) of at least 20 microns, more preferably at least 40 microns, or even at least 60 microns, typically up to about 300 microns, or even up to 200 microns or even up to 150 microns. Highly preferred materials have an average thickness of about 70 microns to 100 microns.

Preferred elastic materials include VFE-CD, available from Tredegar Industries Inc. of Terre Haute, Ind., USA, and L-86, L-89, or L-90, available from Fulflex (Limerick, Ireland).

The longitudinal side edges of the topsheet are preferably joined or attached to the longitudinal side edges of the backsheet, by any attachment means known in the art, to form longitudinally opposing attachment areas. In one preferred embodiment of the present invention, the topsheet and the backsheet are attached to one another in some locations and are indirectly joined together in other locations.

Preferably, the absorbent article of the invention is sag-tolerant, and has preferably a topsheet that is sag-tolerant. This means that the topsheet does not sag and that the topsheet keeps its z-direction alignment with the anal region and genitals of the wearer, and typically also its x and y direction alignment, when the backsheet and absorbent core sag due to increased weight of the body exudates received by the article. The absorbent article, preferably diaper or training pants, has means to ensure that the topsheet stays in about the same contact or close proximity with the wearer's anal and/or genital region when the backsheet and core sag, compared to just after application of the article to the wearer, when the backsheet and core do not yet sag. Typically, the topsheet is sag-tolerant to such an extent that when the geometrical centre point of the backsheet is pulled down 4 cm, the topsheet does not move down more than 0.5 cm, or even not more than 0.25 cm, or typically the topsheet does not move down at all, and/or such that the longitudinal side edges of the opening do not move in the x and y direction more than 0.5 cm, or preferably not more than 0.25 cm, or do not move at all.

Preferably, the average width of the topsheet, including the width of the opening, is larger than the average distance between the longitudinal attachment areas of the topsheet to the backsheet, mentioned above. Also it is preferred that the average width of the topsheet, including the width of the opening, is larger than the average width of the backsheet. The topsheet may for example have one or more transverse and/or, more preferably, longitudinal folds, which can unfold in use and allow sagging of the core and backsheet, while the topsheet remains in place.

The topsheet material may be liquid or urine-pervious or impervious. It may be preferred that the topsheet material is liquid or urine-pervious in one direction, but liquid or urine-impervious in the opposite direction, i.e., that body fluids may penetrate through the topsheet to the remaining part of the diaper, but that no or limited amounts of liquid (urine) can penetrate in the reverse direction, toward the wearer's skin.

However, in a highly preferred embodiment, the topsheet or at least more than 50% of its surface area (that faces the wearer in use) is hydrophobic. It is preferred that the topsheet is urine-impermeable and feces-impermeable, except for the opening. The topsheet is for example made of a material having a Strike Through time for the first gush of more than 120 seconds, as determined by the test method described above. Preferred topsheet materials are considered urine-impermeable feces-impermeable and thus suitable, when they have a low surface energy and a uniform pore size distribution, preferably with the low surface energy values, pore sizes and air permeability values described in EP 1 417 945. Preferred are materials with an alcohol repellency of at least 7 or more preferably at least 8 or even more preferably at least 9, or even more preferably at least 10; preferably having a surface energy of less than 25 mN/m; preferably having a contact angle with water of above 130°; and preferably having a mean pore size of less than 20 microns, preferably less than 17 microns, or most preferably less than 13 microns, but preferably at least 2 microns, or preferably at least 5 microns. Preferably, the topsheet has an air permeability of at least 3 Darcy, or preferably at least 10 Darcy, or even more preferably at least 20 Darcy, or even more preferably at least 30 Darcy, or most preferably at least 50 Darcy.

Preferred topsheets are made of hydrophobic material or are treated to be hydrophobic (in order to isolate the wearer's skin from liquids contained in the remaining part of the diaper), with for example a hydrophobic surface coating. Preferred hydrophobic surface coatings are for example described in co-pending application U.S. 60/543,785, filed Feb. 11, 2004. Preferably, the hydrophobic surface coating comprises one or more silicone polymers or fluorinated polymers. Suitable silicone polymers are for example selected from the group consisting of silicone MQ resins, polydimethysiloxanes, crosslinked silicones, silicone liquid elastomers, and combinations thereof. Typically, the molecular weight of such silicone polymers should be at least about 4000 MW, preferably at least about 10,000 MW, more preferably at least about 15,000 MW, even more preferably at least about 20,000 MW, and most preferably at least about 25,000 MW. Preferred polydimethylsiloxanes are selected from the group consisting of vinyl-terminated polydimethsiloxanes, methyl hydrogen dimethylsiloxanes, hydroxyl-terminated polydimethysiloxanes, organo-modified polydimethylsiloxanes, and combinations thereof. Suitable fluorinated polymers are selected from the group consisting of telomers and polymers containing tetrafluoroethylene and/or perfluorinated alkyl chains. For instance, fluorinated surfactants, which are commercially available from DuPont, Wilmington, Del., USA under the trade name ZONYL, are suitable for use. In particular, ZONYL 321, 329, 8740, 9027, and 9360 are well suited for use in the present invention. Additionally, other ZONYL materials include fluoradditives like micro-powders may be useful. These include, but are not limited to ZONYL MP1100, MP1200, MP1400, MP1500J, MP1600N, TE-3667N (which is a water dispersion). Preferably, the coating is free of aminosilicones.

These materials are preferably deposited onto the topsheet in amounts of at least about 0.01 gsm (gram of material/square meter of topsheet), more preferably at least about 0.05 gsm, and most preferably at least about 0.1 gsm.

A suitable topsheet may be manufactured from a wide range of materials, including woven or nonwoven webs of natural fibers (e.g., wood or cotton fibers) or synthetic fibers (e.g., polyester, polyethylene and/or polypropylene fibers), or a combination of natural and synthetic fibers. If the topsheet includes fibers, the fibers may be for example spunbond, carded, wet-laid, meltblown, hydroentangled, or otherwise processed as is known in the art.

Preferred are materials that are compliant, soft feeling, and non-irritating to the wearer's skin.

Highly preferred are webs comprising spunbond layers (S) and one or more meltblown layer(s) (M), wherein the surfaces of the web are formed by spunbond layer(s). Preferred are such webs with a relatively high basis weight, for example more than 25 gram/m$^2$ (gsm), for example 34 gsm SMMS (two 12 gsm meltblown layers and two 5 gsm spunbond layers); 34 gsm SMMS (two 10 gsm meltblown layers and two 7 gsm spunbond layers); 30 gsm SMMS (two 10 gsm meltblown layers and two 5 gsm spunbond layers); 30 gsm SMMS (two 8 gsm meltblown layers and two 7 gsm spunbond layers); 34 gsm SMS (one 20 gsm meltblown layer and two 7 gsm spunbond layers), or for example webs comprising two layers of 17 gsm SMMS, as described above.

Any portion of the topsheet may be coated with a lotion or powder, known in the art. It may be preferred that at least lotion is present on the primary elasticated areas, and even preferably on the secondary elasticated areas. The lotion used on one elasticated area may be different from the lotion used on another elasticated area, or on the remaining part of the topsheet. Examples of lotions include those described in U.S. Pat. No. 5,607,760, U.S. Pat. No. 5,609,587, U.S. Pat. No. 5,635,191, U.S. Pat. No. 5,643,588, and WO 95/24173, provided the lotion is compatible with the elastic material, and does not destroy the elastic material or reduce its elasticity.

The absorbent article also comprises a typically liquid-impervious backsheet, as known in the art. In preferred embodiments, the liquid-impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind., USA and sold under the trade names X15306, X10962 and X10964. The backsheet, or any portion thereof, may be elastically extendable in one or more directions.

The backsheet may be attached or joined to the topsheet, the absorbent core, or any other element of the diaper by any attachment means known in the art. It may be highly preferred that the longitudinal side edges of the topsheet and backsheet are directly attached to one another, but that the longitudinal edges of the topsheet and the core are not attached to one another.

The attachment means to attach the topsheet and the backsheet, and also the genital coversheet may include a uniform continuous layer of adhesive, a patterned layer of adhesive, or an array of separate lines, spirals, or spots of adhesive, such as disclosed in U.S. Pat. No. 4,573,986. Adhesives that have been found to be satisfactory are manufactured by H. B. Fuller Company of St. Paul, Minn., USA and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core may comprise any absorbent material which is generally compressible, conformable, non-irritating to the wearer's skin, and capable of absorbing and retaining urine, such as: comminuted wood pulp; creped cellulose wadding; meltblown polymers, including coform; chemically stiffened, modified or cross-linked cellulosic fibers; tissue, including tissue wraps and tissue laminates; absorbent foams; absorbent sponges; super absorbent polymers; absorbent gelling materials; or any other known absorbent material or combinations of materials; absorbent cores may be preferred which have an absorbent storage layer which comprises more than 80% by weight of the absorbent core content (e.g., excluding core wrap) of absorbent gelling material, and which is preferably free of airfelt.

The absorbent article may also include a sub-layer (which may be the same as the body-facing liner described above) disposed between the topsheet and the absorbent core, capable of accepting, and/or immobilizing bodily exudates, typically such as fecal material. Suitable materials for use as the sub-layer may include large cell open foams, macroporous compression resistant highloft nonwovens, large size particulate forms of open and closed cell foams (macro and/or microporous), highloft nonwovens, polyolefin, polystyrene, polyurethane foams or particles, structures comprising a multiplicity of vertically oriented, preferably looped, strands of fibers, or preferably apertured formed films, as described above with respect to the genital coversheet.

The absorbent article is preferably a disposable adult or infant diaper or training pants/pull-on pants. Diapers or training pants of the invention may have side panels, and/or more preferably one or more pairs of elasticated leg cuffs that provide improved containment of liquids and other body exudates. Leg cuffs may also be referred to as leg bands, side flaps, barrier cuffs, or elastic cuffs, as described in U.S. Pat. No. 3,860,003, U.S. Pat. No. 4,808,178, U.S. Pat. No. 4,695,278 and U.S. Pat. No. 4,795,454.

The diapers preferably have a fastening system, typically joined to the waistband, as known in the art. Preferred fastening systems comprise fastening tabs and landing zones, wherein the fastening tabs are attached or joined to the back region of the diaper and the landing zones are part of the front region of the diaper.

It may be preferred that the articles of the invention (e.g., diapers) when packed in their packaging material, comprise two transverse folds, so that when unfolded for use by the user or care taker, the article (e.g., diaper) is in a U-shape and easier to apply.

Preferred Processes to Make a Diaper of the Invention

A topsheet with an opening, typically along its longitudinal axis, and primary elasticated areas and a genital coversheet is obtained as follows.

A longitudinally extending (slit) opening may be formed (cut) in the topsheet material first and a pair of primary elastic bands may then be attached, in a stretched state, to the topsheet, so that an elastic band is present adjacent or in close proximity to each longitudinal edge of the opening. Alternatively, the primary elastic bands may be first attached to the topsheet in a stretched state, extending longitudinally over the topsheet, for example in an X-shape, after which a longitudinally extending (slit) opening is formed (cut) through part of the topsheet material and part of the elastic bands, typically along the longitudinal axis of the topsheet material and the strands or bands.

Preferred adhesives for attaching the primary elastic strands or bands include H2031, available from Bostik (Greenville, S.C., USA) and HL-1620 available from H.B. Fuller (St. Paul, Minn., USA).

In a non-limiting example, two elastic bands of L-89 elastic material, available from Fulflex, with (in relaxed state) a thickness of about 0.1 mm, a width of 20 mm and a length of 17 cm, are obtained and also a sheet of a polypropylene nonwoven material, which is 20-25 cm wide and 50-55 cm long, such as available from BBA, Fibertex or Pegas.

In the stretched state, a slit opening with a length of between 25 cm and 35 cm, typically about 31 cm to 33 cm is cut in the nonwoven. This may be cut as a slit, whereby the slit opening obtains its width due to the spreading elasticated areas, or the slit opening may be cut with a width dimension, for example up to 4.0 cm. Typically, the slit opening is cut as a slit without a width dimension, but in the front region of the topsheet, at the front point of the slit opening, an additional diamond-shaped cut is made, as can be seen in FIG. 4.

If the elasticated areas are present on the surface of the topsheet which is in contact with the skin of the user, it may be preferred that an additional layer, e.g., nonwoven material, is placed on the elastic areas, to avoid direct contact by the elastic areas with the skin.

One elastic band is glued in a partially stretched state to each longitudinal edge of the opening of the nonwoven. This is for example done such that the centre 9 cm of the elastic band is stretched 336%, and the end portions of each 4 cm are maintained in an unstretched state. Each elastic band is then glued on the nonwoven in a manner that the front end region of one elastic band bends away from the front end region of the opposing elastic band, and the back end region of one elastic band bends away from the back end region of the opposing elastic band, in the shape of an X. This is done such that, after application, the transverse distance between the inner two edges of the front end regions and of the back end regions is for example 80 mm in the stretched state. The distance between the centre points of the elasticated areas is for example only 40 mm.

The angle of the front end region with the line through the centre portion and parallel to the longitudinal axis of the topsheet, as described above and identified in FIG. 2 and FIG. 3 as angle α, is for example, about 10° to 40°, as described herein. The angle of the back end region, as described above and identified in FIG. 2 as angle β, is also for example, about 10° to 40°.

The genital coversheet is attached to the topsheet in a stretched state, such that the front 15% to 30% of the maximum length of the opening is covered by the longest part of the genital coversheet. The genital coversheet has preferably a curved or V-shaped edge above the opening. The genital coversheet may for example have the shape shown in FIG. 6, and it may be folded prior to attachment to the topsheet, for example as shown in FIG. 7.

Figure 7:
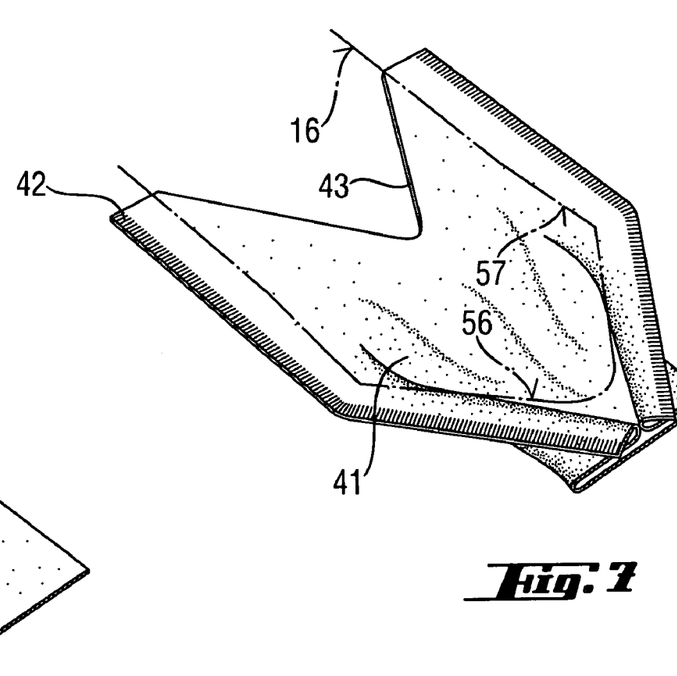
FIG. 7 shows a perspective view of the preferred genital coversheet, folded for incorporation into the absorbent article.

The genital coversheet is for example attached to the surface of the topsheet which is not in contact with the skin of the user, with at least two longitudinal areas (lines, spirals, dots) of adhesive, each being between a longitudinal edge of the topsheet and an elastic band, e.g., spaced about 0.5 to 1.5 cm away from said elastic band, and with a V-shaped attachment area, as shown in FIG. 7. The distance between the two substantially parallel attachment areas is for example at the most about half the width of the genital coversheet between these areas, so that the genital coversheet hangs downwards in use, under the opening, as a pocket for the genitals.

The topsheet may be used on a Pampers Premium Size 4 diaper available from The Procter & Gamble Company, Cincinnati, Ohio, USA, designed for a baby weight range of 21-37 pounds (approximately 9.5 kg-16.8 kg), or it may replace the layer of a Pampers premium Size 4 diaper which is on the absorbent core and in use is in contact with the skin of the baby. In the latter case, the topsheet with the elastic bands is attached to the front and back waistbands, and typically to the longitudinal side edges of the backsheet.

DESCRIPTION OF THE FIGURES

Figure 1:
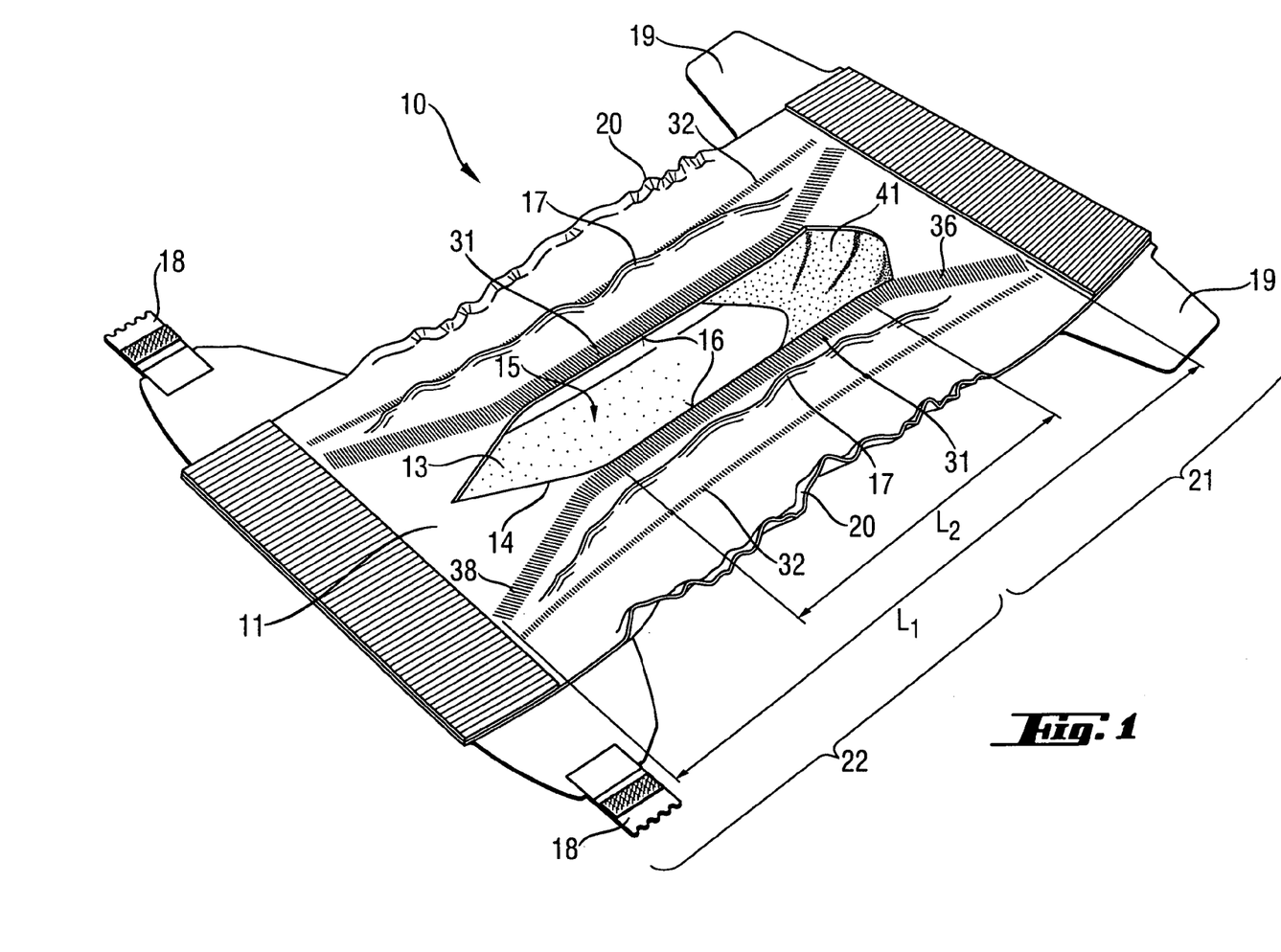
FIG. 1 shows a perspective view of a preferred absorbent article of the present invention, comprising a preferred genital coversheet.

FIG. 1 shows a perspective view of a preferred absorbent article, a diaper (10), of the present invention with a front region (21) and back region (22) and with a genital coversheet (41), placed under the topsheet (11) and under the opening (14) in said topsheet. A void space (15) is present between the absorbent core (13) and the topsheet (11) and between the absorbent core (13) and the genital coversheet (41). In use, the genital coversheet (41) will cover the genitals of the user. Typically, the genital coversheet (41) is configured such that it can form a pocket around the genitals. This is further shown in FIG. 3, discussed below.

The diaper (10) typically comprises also a back waist band with preferably ears with fasteners (18) and a front waist band (19) with receiving areas for the fasteners. Typically, the fasteners comprise hooks and/or adhesive and the receiving areas are preferably formed from loop-containing material.

As described above, the topsheet (11) is typically sag-tolerant and non-elastically extendable and it preferably has one or more transverse folds and/or longitudinal folds (17) to make it sag-tolerant.

The topsheet (11) is elasticated, having primary elasticated areas (31) positioned along the longitudinal side edges (16) of the opening (14). The topsheet (11) may also have secondary elasticated areas (32), or even tertiary elasticated areas (not shown). The primary elasticated areas (31) have each a centre region with a length L2, the centre regions being substantially parallel to one another, whereby L2 is typically about 30% to 70% of the total length L1 of the primary elasticated areas (31), and preferably about 40% to 80% of the maximum length of the opening (14). The primary elasticated areas (31) are preferably arranged in an X-shape, whereby the front end portions (36) bend away from one another and the back end portions (38) bend away from one another.

The diaper (10) typically also comprises elasticated bands along the longitudinal side edges of the diaper (10), so called leg cuffs (20).

Figure 2:
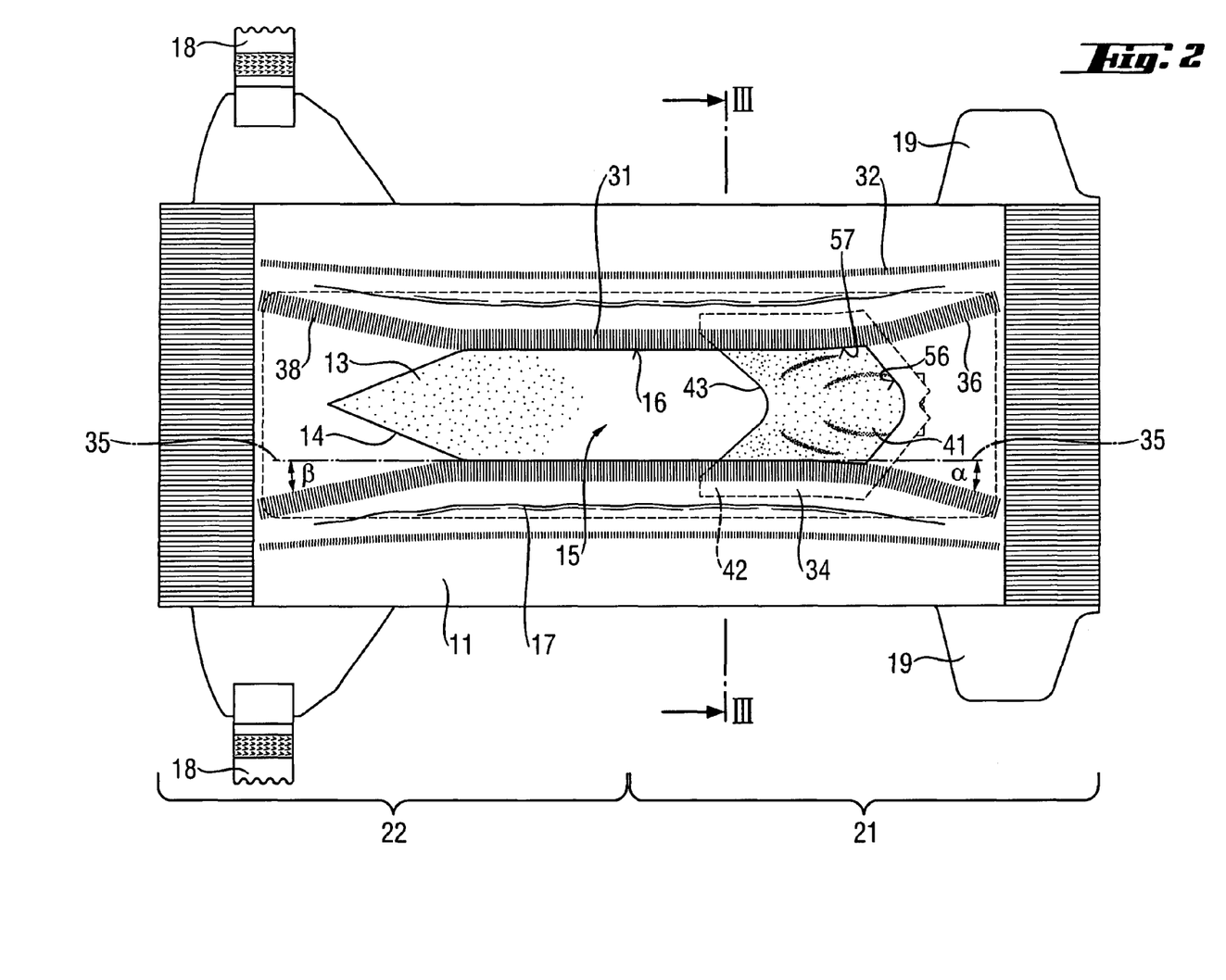
FIG. 2 shows a plan view of the absorbent article of FIG. 1.

FIG. 2 shows a plan (top) view of the diaper (10) of FIG. 1, in a stretched state. The genital coversheet (41) is placed under the topsheet (11) and attached along its longitudinal side edges to the topsheet (11), with attachment areas (42), which are for example in the form of longitudinal lines of adhesive. The attachment areas (42) are typically positioned at least or only along the longitudinal side edges (16) of the opening (14), preferably parallel thereto and parallel to one another. Each attachment area (42) is typically (at least) positioned between a primary elasticated area (31) and the longitudinal side edge of the topsheet, or between the primary elasticated area (31) and the secondary elasticated area (32) (when present), such that the genital coversheet (41) is attached to the topsheet (11) in at least or only the non-elasticated areas (34) of the topsheet (11). It is preferred that the genital coversheet (41) has a transverse edge (43) which is not a straight edge, but instead is curved or arrow-shaped, to make the genital coversheet (41) more comfortable in use.

As shown in FIG. 2, the primary elasticated areas (31) are preferably arranged in the shape of an X, wherein each front end portion (36) of the elasticated area forms an angle α with the longitudinal line (35) parallel to the longitudinal axis of the topsheet and through that part of the elasticated area that is (directly) adjacent to a longitudinal side edge (16) of the opening. This angle α is preferably about 17° to 30° in the stretched state. Each back end portion (38) of the elasticated area similarly forms an angle β which is preferably about 17° to 30° in the stretched state.

Figure 3:
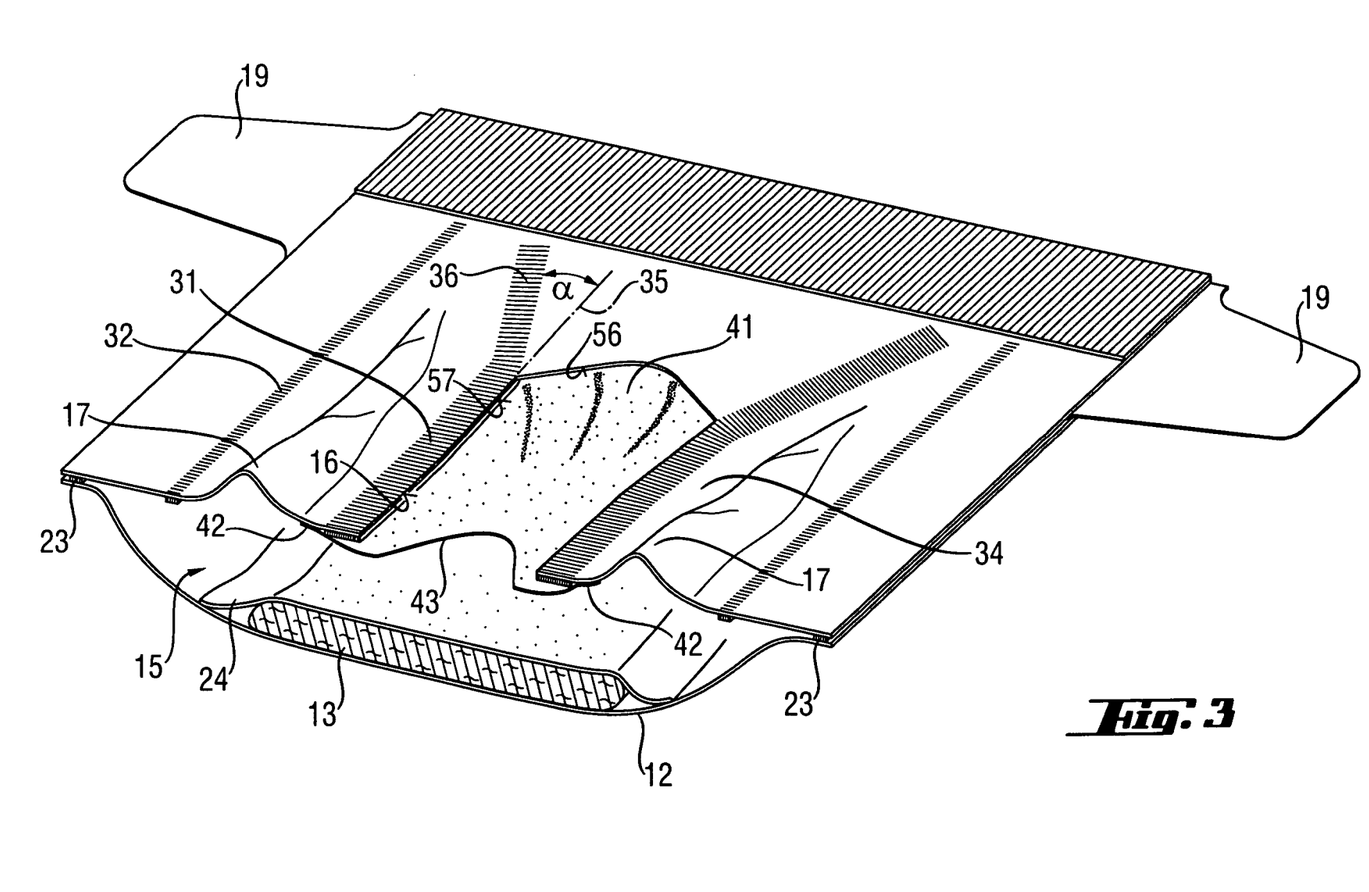
FIG. 3 shows a section view of an absorbent article taken at line III-III in FIG. 2.

FIG. 3 shows a section view of the diaper (10) of FIGS. 1 and 2, taken at line III-III in FIG. 2. It shows the void space (15) between the genital coversheet (41) and the absorbent core (13) and between the topsheet (11) and the absorbent core (13). The topsheet (11) with the longitudinal folds (17) is typically not attached to the absorbent core (13), but directly to the backsheet (12) with longitudinal attachment lines (23), to ensure that the diaper (10) and the topsheet (11) thereof are sag-tolerant. The absorbent core (13) may comprise a specific sub-layer (24), which comprises means to immobilize fecal material, for example a layer with vertically extending (z-direction) fibers, or an apertured web or film, as described herein.

The genital coversheet (41) is typically urine-permeable, as described herein and it may comprise or consist of a material with micropores, such as the apertured webs or films described herein, or for example the carded webs described herein.

The topsheet (11) shown in FIGS. 1, 2 and 3 is preferably made by making a longitudinal slit (58) with preferably no width dimension in the topsheet material and cutting an additional front cut-out section (55) out of the topsheet, said section (55) extending from the front of this slit (58) toward the front of the diaper (10). This is further shown in FIGS. 4 and 5.

Preferably, the front cut-out section (55) is 'diamond-shaped', although it is preferred that the diamond-shaped cut-out section (55) has a front edge (56) which is curved. The side edges (57), extending directly from the slit (58) toward the front edge of the diaper (10) and connecting the curved front edge (56) with the slit (58), preferably intersect at an angle γ, which is preferably between 40° and 140°, more preferably between 55° and 110°.

Figure 6:
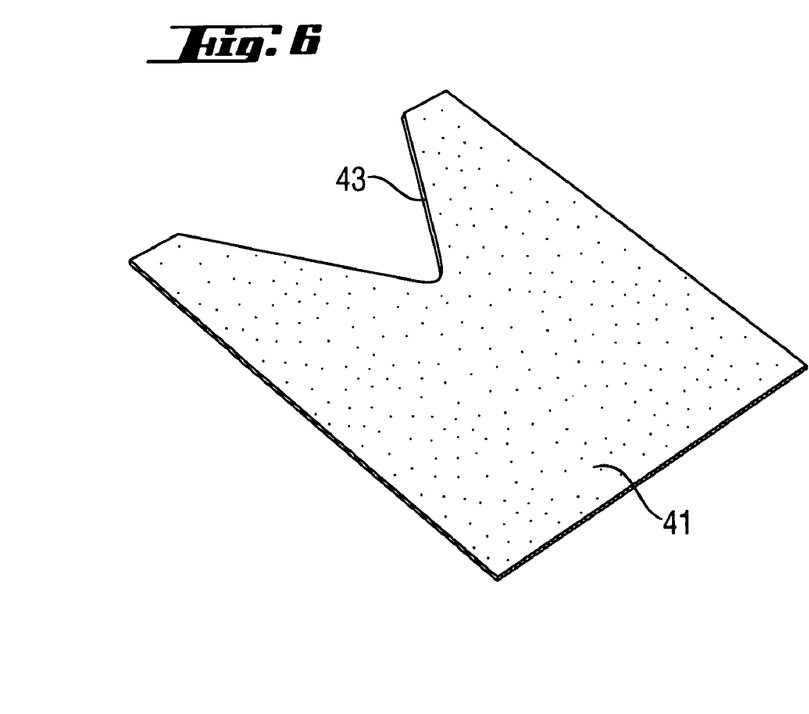
FIG. 6 shows a perspective view of a preferred genital coversheet before incorporation into the absorbent article.

FIG. 6 shows a perspective view of the shape of a preferred genital coversheet (41) of the absorbent article (10) of the invention, before incorporation into the absorbent article (10). The genital coversheet (41) has preferably a rounded or V-shaped 'transverse' edge (43), i.e., the edge (43) being disposed in or under the slit opening (14).

FIG. 7 shows a perspective view of the preferred genital coversheet (41) of FIG. 6, which is folded for incorporation into the diaper (10) of FIGS. 1 to 3, and shows the areas which in the diaper (10) will become the attachment areas (42); said attachment areas (42) may for example comprise adhesive for attachment to the topsheet (11). It is shown in FIG. 7 how, in a preferred embodiment, the genital coversheet (41) will be placed along portions of the longitudinal side edges (16) of the opening (14), but in any event along the edges of the cut-out section (55), including side edges (57) and curved front edge (56).

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications are within the scope of this invention.

What is claimed is:

1. An absorbent article comprising:
    a backsheet;
    a topsheet made of material that is urine impermeable and feces impermeable, the topsheet having an elongate opening therethrough, the elongate opening having a front region and a back region, the elongate opening being continuous and positioned such that when the article is worn by a wearer, the front region is adjacent the wearer's genitals, and the back region will allow exuded fecal material to pass therethrough;
    an absorbent core situated above the backsheet; and
    a urine permeable genital coversheet partially attached to the article forming attached areas and unattached areas, and lying across the elongate opening in the front region in a position to cover the wearer's genitals, but not obstruct the back region, when the article is worn, the genital coversheet having a rearward transverse edge that is unattached to the article and traverses the elongate opening, said rearward transverse edge being spaced above said absorbent core beneath the elongate opening, wherein the genital coversheet is formed of a section of material distinct from a section of material forming the topsheet.

2. The absorbent article as in claim 1, wherein the urine permeable genital coversheet is positioned above the topsheet and so as to be in direct contact with the wearer's skin when the article is worn.

3. The absorbent article as in claim 1, wherein the urine permeable genital coversheet is positioned between the topsheet and the absorbent core, and wherein said coversheet is directly secured to the topsheet.

4. The absorbent article as in claim 1, wherein said topsheet has two opposing inner side edges defining sides of the elongate opening, and portions of the urine permeable genital coversheet are directly secured to the topsheet along said opposing inner side edges and the urine permeable genital coversheet forms a pocket between said opposing inner side edges.

5. The absorbent article of claim 4, wherein the topsheet comprises elasticated areas and non-elasticated areas, and the urine permeable genital coversheet is attached to the topsheet in the non-elasticated areas in a front region of the topsheet.

6. The absorbent article of claim 5, wherein the urine permeable genital coversheet is attached in at least two attachment areas, at least one of the attachment areas being disposed along one inner side edge and another of the attachment areas being disposed along the other inner side edge, the average width of the urine permeable genital coversheet between said two attachment areas being larger than the average distance between said two attachment areas.

7. The absorbent article of claim 1, wherein the topsheet has two opposing inner side edges and forward and rearward edges defining the elongate opening, and at least portions of the two opposing inner side edges have first and second elasticated areas therealong.

8. The absorbent article of claim 7, wherein the respective first and second elasticated areas extend forward on the topsheet beyond the forward edge.

9. The absorbent article of claim 7, wherein the respective first and second elasticated areas extend rearward on the topsheet beyond the rearward edge.

10. The absorbent article of claim 7, wherein the respective first and second elasticated areas extend forward on the topsheet beyond the forward edge, and rearward on the topsheet beyond the rearward edge.

11. The absorbent article of claim 1, wherein the urine permeable genital coversheet is extendable and is configured to form a pocket for the genitals when worn.

12. The absorbent article as in claim 1, wherein the urine permeable genital coversheet comprises a spunbond nonwoven web, carded nonwoven web, or a formed film.

13. The absorbent article as in claim 1, wherein a maximum length of the portion of the urine permeable genital coversheet that is present across the aperture is from 10% to 50% of a maximum length of the aperture.

14. The absorbent article as in claim 1, wherein the absorbent article is sag-tolerant, and the topsheet has one or more longitudinal folds.

15. The absorbent article as in claim 1, wherein the absorbent article is an adult diaper or infant diaper or training pants.

16. The absorbent article as in claim 1, wherein the urine permeable genital coversheet comprises a carded nonwoven with an average caliper measured under compression of 0.3 psi of at least 0.3 mm and with a mean pore size of from 100 microns to 300 microns.

17. An absorbent article comprising:

a backsheet;

a topsheet terminating at a front waist band at a front end and terminating at a back waist band at a back end, the topsheet being made of material that is urine impermeable and feces impermeable, the topsheet having an elongate opening therethrough, the elongate opening having a front region and a back region, the elongate opening being continuous and defined by opposing longitudinal side edges and forward and rearward edges, and being positioned such that when the article is worn by a wearer, the front region is adjacent the wearer's genitals, and the back region will allow exuded fecal material to pass therethrough;

a urine permeable genital coversheet partially attached to the article forming attached areas and unattached areas, and lying across the elongate opening in the front region in a position to cover the wearer's genitals, but not obstruct the back region, when the article is worn, the genital coversheet having a rearward transverse edge that is unattached to the article and traverses the elongate opening, said rearward transverse edge being spaced above said absorbent core beneath the elongate opening, wherein the genital coversheet is formed of a section of material distinct from a section of material forming the topsheet;

a primary pair of respective primary first and second elongate elastic bands or elastic strands disposed on the topsheet along the respective opposing longitudinal side edges, each of the first and second elongate elastic bands or elastic strands respectively extending rearward beyond the rearward edge toward the rear waist band and forward beyond the forward edge toward the front waist band, and not meeting each other;

a secondary pair of respective secondary first and second elongate elastic bands or elastic strands disposed on the article laterally outside of the primary pair; and an absorbent core situated above the backsheet;

wherein no elastic band or elastic strand is disposed on the topsheet along the respective forward or rearward edge of the elongate opening, that meets with both of said primary first and second elongate elastic bands or elastic strands, and also traverses a longitudinal axis of the topsheet.

* * * * *